(12) United States Patent
Duplaga et al.

(10) Patent No.: US 11,008,454 B2
(45) Date of Patent: May 18, 2021

(54) HOT-MELT ADHESIVE COMPOSITION FOR ELASTIC ATTACHMENTS

(71) Applicant: Bostik SA, Colombes (FR)

(72) Inventors: Urszula Duplaga, Bienville (FR); Naji Hussein, Compiegne (FR)

(73) Assignee: Bostik SA, Colombes (FR)

( * ) Notice: Subject to any disclaimer, the term of this patent is extended or adjusted under 35 U.S.C. 154(b) by 32 days.

(21) Appl. No.: 16/468,019

(22) PCT Filed: Dec. 19, 2017

(86) PCT No.: PCT/EP2017/083541
§ 371 (c)(1),
(2) Date: Jun. 10, 2019

(87) PCT Pub. No.: WO2018/114949
PCT Pub. Date: Jun. 28, 2018

(65) Prior Publication Data
US 2019/0382577 A1 Dec. 19, 2019

(30) Foreign Application Priority Data

Dec. 21, 2016 (EP) .................................... 16306761

(51) Int. Cl.
*C08L 53/02* (2006.01)
*C09J 153/02* (2006.01)

(52) U.S. Cl.
CPC .............. *C08L 53/02* (2013.01); *C09J 153/02* (2013.01); *C08L 2205/025* (2013.01); *C08L 2205/035* (2013.01); *C09J 2203/00* (2013.01)

(58) Field of Classification Search
CPC .............. C08L 53/02; C08L 2205/025; C08L 2205/035; C09J 153/02
See application file for complete search history.

(56) References Cited

U.S. PATENT DOCUMENTS

| | | |
|---|---|---|
| 6,967,178 B2 | 11/2005 | Zhou et al. |
| 2009/0133834 A1 | 5/2009 | Lechat et al. |
| 2012/0258246 A1 | 10/2012 | Saine et al. |
| 2015/0203725 A1 | 7/2015 | Stafeil et al. |

FOREIGN PATENT DOCUMENTS

| | | |
|---|---|---|
| EP | 2980179 A1 | 2/2016 |
| WO | 2009026085 A1 | 2/2009 |
| WO | 2014175410 A1 | 10/2014 |
| WO | 2014189150 A1 | 11/2014 |

OTHER PUBLICATIONS

ISA/EP; International Search Report and Written Opinion for International Patent Application No. PCT/EP2017/083541 dated Feb. 22, 2018, 10 pages.

*Primary Examiner* — Jeffrey C Mullis
(74) *Attorney, Agent, or Firm* — NK Patent Law

(57) ABSTRACT

The present invention relates to a hot-melt adhesive composition comprising at least one particular mixture of SBC, at least one tackifying resin, at least one wax, and at least one plasticizer. The present invention also relates to a laminate comprising the hot-melt adhesive composition according to the invention that can be used to manufacture disposable hygiene articles.

13 Claims, 1 Drawing Sheet

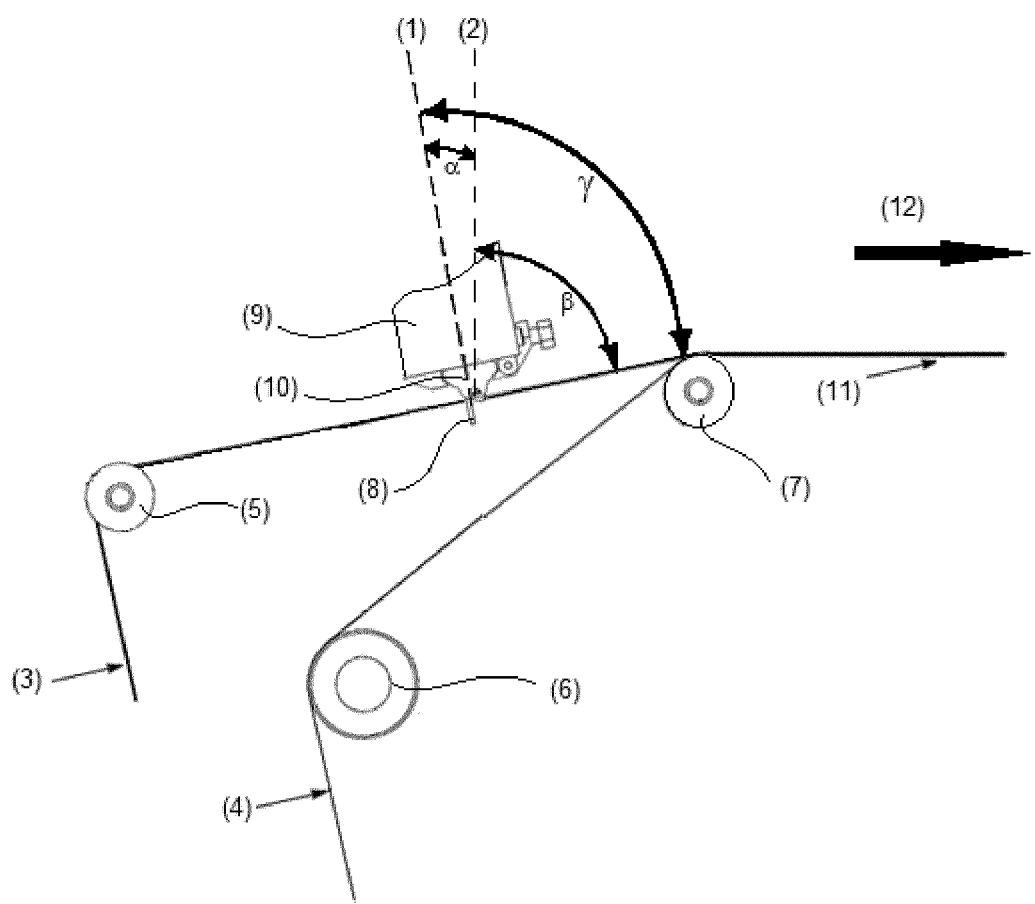

HOT-MELT ADHESIVE COMPOSITION FOR ELASTIC ATTACHMENTS

CROSS-REFERENCE TO RELATED APPLICATIONS

This application is a U.S. National Stage application of International Application No. PCT/EP2017/083541, filed on 19 Dec. 2017, which claims the benefit of European Patent Application No. 16306761.4, filed 21 Dec. 2016.

FIELD OF THE INVENTION

The present invention relates to a hot-melt adhesive composition comprising at least one particular mixture of styrene block copolymers (SBC), at least one tackifying resin, at least one wax, and at least one plasticizer, and its use for elastic attachment applications.

The present invention also relates to a laminate comprising the hot-melt adhesive composition according to the invention that can be used to manufacture disposable hygiene articles.

BACKGROUND OF THE INVENTION

Disposable hygiene articles are made from a wide variety of substrates (non-woven, elastomeric material, film, such as polyolefin film and in particular polyethylene or polypropylene film) bonded with adhesive materials. Among examples of disposable hygiene articles, mention may be made of diapers, napkins or adult incontinence disposable articles.

The disposable hygiene articles are produced at high speed line rates. In such production, hot melt adhesives are typically used because they can be easily applied to substrates (at the molten state) and rapidly develop strong bond upon cooling, without any additional manufacturing steps such as solvent removal.

Hot melt adhesives are used in the diaper manufacturing industry to bond a wider variety of substrates within a broader adhesive application process window.

Generally, several kinds of hot melt adhesives can be found in disposable hygiene articles, depending on their emplacement and final function, such as:
- Core adhesives: used to keep in place the diaper core (fluff and SuperAbsorbentPolymer "SAP"), during the manufacture of the diaper but also during the use of the diaper mainly after that said diaper has been wet.
- Construction adhesives: which bind the polyethylene back sheet to the nonwoven substrates or which bind two nonwoven substrates.
- Elastic adhesives: used to bind elastic material (such as polyurethane based strands) to sheet-like substrates (such as polyethylene "PE" or to polypropylene "PP" and Nonwoven substrates).

Depending on the aimed application, the hot melt adhesive should comply with some minimal requirements relative to its end-use and its application (coating) process.

In particular, the hot melt adhesive should display good processability.

Usually, the molten adhesive is sprayed, fiberized or coated on cylindrical or plane surface. Once cooled down, the adhesive needs to fulfill multiple requirements, like bond strength measured by peel force or bond retention under or after mechanical stress, and under or after various thermal conditions.

In particular, in elastic attachment applications, the adhesive should maintain the elastic material in place, particularly when solicited during manufacturing and use of the disposable hygiene article. Indeed, during the manufacture process, the elastic material (for example a set of elastic strands) is usually first stretched prior to bonding and then the adhesive is applied onto the elastic material, either by non-contact (spraying) or contact applications, then the elastic material coated with the adhesive are quickly laminated between two sheet-like substrates (for example a nonwoven substrate and a polyolefin film). After that, the elastic material is permitted to relax, creating a gathered (or rushed) laminate having substantial flexibility. The adhesive thus needs to present high cohesion and elasticity to be resistant enough to creep strength. Moreover, in order to avoid any adhesive failure, good adhesion on the elastic material is also recommended.

Today the market trend is moving toward the production of better quality diapers at higher speed line productivity and reduced cost. To meet this need, higher-speed diapers machines have been developed in the hygiene industry and different ways of cost reduction have been sought.

One possible way of lowering the production costs is using thinner substrates. However, thinning of plastic substrate such as polyethylene film raises heat damage issues as the hot-melt adhesive is usually applied on the substrate at high temperature (at least 150° C.). In particular, application of the hot-melt adhesive at such temperature on polyethylene film can cause "burn through" problems, such as melting of the substrate or formation of wrinkles on the substrate.

Another possible way of lowering the production costs is applying the hot-melt adhesive at a lower temperature (lower than 150° C., such as 130° C.-140° C.). However, lowering the application temperature increases the hot-melt adhesive viscosity and usually leads to poor processability of the adhesive at low temperature.

In particular, when the production lines reach a 400 meter per minute (m/mn) or higher speed, high pressure levels exceeding the pressure alarm limit are often observed in the pumps and pipes of the coating systems, inducing line shutdown and/or variability of the coated adhesive add-ons.

Moreover, it was observed that the current hot melt adhesives lead to irregular adhesive patterns under continuous or intermittent application process at such line speed. In particular, adhesive scattering at the nozzle exit, build up, poor wrapping of the elastic strand and bad spiral pattern were observed when using different types of continuous or intermittent, contact or non-contact, application processes.

All these problems largely reduce the production line efficiency as they require line stop, line cleaning and maintenance and waste management at start & stop, and also increase the rate of non-conforming end-products for example due to bad patterns or poor bond performances. In this context, it is thus very important that the production lines are not stopped because of issues related or induced by the hot melt adhesive.

Various patent literatures teach to use low softening point tackifier, or less polymer content and more plasticizer to obtain a low temperature applicable hot-melt adhesive, for example to avoid "burn through" phenomenon in case of thinner substrates or thermally sensitive substrates such as polyolefin substrates. However, this often led to negative cohesion and deterioration of creep resistance of the adhesive. Also, the processability of these adhesives was not suitable for high line speed of at least 400 m/mn and intermittent application mode.

WO 2014/175410 (Henkel Ag & Co KGAA) deals with a hot-melt adhesive composition comprising a blend of thermoplastic block copolymers of vinyl aromatic hydrocarbons and conjugated diene compounds, comprising: (A1) a radial type styrene block copolymer having a styrene content of 35 to 45% by weight and a diblock content of 50 to 90% by weight, and having a viscosity at 25° C. as 25% by weight toluene solution of not more than 250 mPa·s., and (A2) a styrene block copolymer having a styrene content of less than 30% by weight, and having a viscosity at 25° C. as 25% by weight toluene solution of more than 250 mPa·s, and a tackifying resin. The composition is taught to be capable to be applied at low temperature (not higher than 140° C.) and to display an excellent adhesiveness to a polyolefin substrate, to be used to manufacture a disposable product.

However, this document does not describe the hot-melt adhesive composition according to the present invention. Neither does it mention the use of a lamination process at a high speed line of at least 400 m/mn. As mentioned above, the use of such high speed line process can raise new problems compared to the use of conventional lower speed application process.

Therefore, there is a real need for Elastic Attachment adhesive offering stable and good performances with enhanced processability at high speed, and which should also be compatible with the new generation of thinner substrates and contact and non-contact application technologies.

It has now been found that it is possible to develop SBC based adhesive, which can be applied at a low temperature (avoiding avoid "burn through" phenomenon) with excellent processability at high speed line (of at least 400 m/mn), which exhibits good coating and adhesive properties for elastic attachment to different substrates and which can provide as well good adhesive pattern control under various application processes.

As mentioned above, one of the advantages of the hot-melt adhesive composition according to the invention is that it can be used at high speed line (of at least 400 m/mn) at a relatively low temperature (as low as 130° C.) and low pressure, and thus enable to avoid maintenance issues and downtime production lines.

Indeed, the hot-melt adhesive composition according to the invention displays excellent processability on high speed coating systems (at a speed rate of at least 400 m/mn and up to 600 m/mn) intended to be used to manufacture disposable hygiene articles without inducing line shutdown (which usually occurs when pump or pipe pressure level reaches or exceeds a maximum limit pressure) and/or without inducing variability of the coated adhesive add-ons.

The word "processability" as used herein corresponds to the ability to melt, pump and transport easily the molten adhesive material to the final location where the bond is required without exceeding the pressure limit in the pumping system (which is usually of 60 bar or above) of standard coating systems, such as those usually used to manufacture disposable hygiene articles, and as further illustrated in the examples.

As mentioned above, another advantage of the hot-melt adhesive composition according to the invention relates to its adhesive properties.

The hot-melt adhesive composition according to the invention displays a good compromise between retention force (cohesion) and adhesion (tackiness) to different substrates (Non-Woven (NW) substrates, Polyolefines such as PE or PP, elastic material such as elastic strands) under various application process, such as those of continuous or intermittent, contact or non-contact coating systems usually used to manufacture disposable hygiene articles.

In particular, it was found that the hot-melt adhesive composition according to the invention enables to manufacture laminates, under contact or non-contact application process, with an excellent creep resistance or bond retention (of at least 75%). In particular, the hot-melt adhesive composition of the invention provides an initial creep resistance of more than 75%, preferably ranging from 80 to 95%.

It was observed that these properties were maintained over time (at room temperature (23° C.) or higher temperature), as illustrated in the examples. In particular, the long term performance of the hot-melt adhesive according to the invention remained roughly unchanged even after ageing for long periods (up to 2-4 weeks at room temperature or at higher temperature (up to 55° C.)).

As mentioned above, another advantage of the hot-melt adhesive composition according to the invention relates to its good coating properties and its good adhesive patterns control, under various application process. These properties are important to get consistent coating results.

It was found that the hot-melt adhesive composition according to the invention provides regular patterns and/or neat cut-offs, under continuous or intermittent application mode.

In particular, it was found that the hot-melt adhesive composition according to the invention can be applied in the desired amount and at the desired location where the bond is required at high speed (>400 m/min) and at low temperature (130-140° C.), under continuous or high intermittent frequency mode, using standard coating systems.

In particular, the hot-melt adhesive composition of the invention provides stable and good wrapping of elastic strands at high line speed.

It has also been found that the hot-melt adhesive composition according to the invention can be used at high speed, as well as at lower speed manufacturing lines of disposable hygiene products, without raising any problems in terms of processability, pattern control, coating property or adhesive performance.

In another aspect, the hot-melt adhesive according to the invention also exhibits a high cold flow resistance, at room temperature (23° C.), and is thus easier to handle and to store.

In another aspect, it was found that the hot-melt adhesive according to the invention is less sensitive to the variation of configuration of the application system, in particular with respect to the contact angle between the adhesive discharger axis and the surface of the substrate to be coated.

Further features and advantages of the invention will appear from the following description of embodiments of the invention, given as non-limiting examples.

SUMMARY OF THE INVENTION

A first object of the invention is a polymer mixture comprising:
at least one thermoplastic styrene block copolymer (A) (designated "SBC (A)") comprising:
at least one radial type styrene block copolymer (A1) (hereinafter noted "radial type SBC (A1)") and
at least one styrene diblock copolymer (A2) (hereinafter noted "diblock (A2)"), with:
a styrene content of at least 30% by weight, based on the total weight of SBC (A), and
a non-zero diblock (A2) content of less than 50% by weight, based on the total weight of SBC (A), at least one thermoplastic styrene block copolymer (B) (designated "SBC (B)") comprising:
  at least one linear type styrene block copolymer (B1) (hereinafter noted "linear type SBC (B1)") and
  at least one styrene diblock copolymer (B2) (hereinafter noted "diblock (B2)") with:
    a styrene content of at least 35% by weight, based on the total weight of SBC (B), and
    a diblock (B2) content of at least 50% by weight, based on the total weight of SBC (B).

Preferably, SBC (A) has:
  a styrene content ranging from 30 to 50% by weight, based on the total weight of SBC (A),
  a diblock (A2) content ranging from 20 to 49% by weight, based on the total weight of SBC (A), and
  a viscosity at 25° C. as a 25% by weight toluene solution of more than 250 mPa·s and up to 500 mPa·s.

More preferably, SBC (A) has:
  a styrene content ranging from 35 to 45% by weight, based on the total weight of SBC (A),
  a diblock (A2) content ranging from 22 to 45% by weigh, based on the total weight of SBC (A), and
  a viscosity at 25° C. as a 25% by weight toluene solution of ranging from 300 to 500 mPa·s, even more preferably ranging from 300 to 450 mPa·s.

Preferably, SBC (B) has:
  a styrene content of at least 40% by weight, based on the total weight of SBC (B),
  a diblock (B2) content ranging from 55 to 80% by weight, based on the total weight of SBC (B), and
  a viscosity at 25° C. as a 25% by weight toluene solution of 200 mPa·s or less, preferably ranging from 100 to 200 mPa·s.

More preferably, SBC (B) has:
  a styrene content ranging from 40 to 55% by weight, based on the total weight of SBC (B),
  a diblock (B2) content ranging from 60 to 70% by weight, based on the total weight of SBC (B), and
  a viscosity at 25° C. as a 25% by weight toluene solution ranging from 100 to 200 mPa·s.

Preferably, the weight ratio of SBC (A) over SBC (B) ranges from 0.5 to 2.5, preferably from 1 to 2.

Preferably, the polymer mixture according to the invention is a thermoplastic styrene block copolymer mixture.

Preferably, the overall styrene content of the above-mentioned polymer mixture represents at least 40% by weight of the total weight of said polymer mixture, and the overall styrene diblock copolymer content of the above-mentioned polymer mixture represents from 30 to 60% by weight of the total weight of said polymer mixture.

More preferably, the overall styrene content of the above-mentioned polymer mixture represents from 40 to 45% by weight of the total weight of said polymer mixture, and the overall styrene diblock copolymer content of the above-mentioned polymer mixture represents from 34 to 55% by weight of the total weight of said polymer mixture.

More preferably, SBC (A) and (B) are both styrene-butadiene based block copolymers, meaning that each of the styrene block copolymers included in SBC (A) and (B), in particular (A1), (A2), (B1) and (B2), comprise at least one non elastomeric block being polystyrene and at least one elastomeric block being polybutadiene.

A second object of the invention is a hot-melt adhesive composition comprising besides the ingredients of the above-mentioned polymer mixture according to the invention:
  at least one tackifying resin (C),
  at least one wax (D), and
  at least one plasticizer (E).

In one embodiment, the total amount of SBC (A) and (B) ranges preferably from 15 to 35% by weight, more preferably from 18 to 35% by weight, even more preferably from 20 to 30% by weight, based on the total weight of the hot-melt adhesive composition according to the invention.

In particular, SBC (A) and (B) can be mixed in any weight ratio within the above mentioned range of amount within the hot-melt adhesive composition. Preferably, the weight ratio of SBC (A) over SBC (B) ranges from 0.5 to 2.5, preferably from 1 to 2.

In another embodiment, the amount of tackifying resin (C) ranges from 35 to 65% by weight, the amount of wax (D) ranges from 0.5 to 5% by weight, the amount of plasticizer (E) ranges from 5 to 25% by weight, based on the total weight of the hot-melt adhesive composition according to the invention.

More preferably, the hot-melt adhesive composition, comprises:
  from 15 to 35% by weight, preferably from 18 to 35% by weight, more preferably from 20 to 30% by weight, of the above-mentioned polymer mixture including SBC (A) and (B),
  from 35 to 65% by weight of at least one tackifying resin (C),
  from 0.5 to 5% by weight of at least one wax (D),
  from 5 to 25% by weight of at least one plasticizer (E),
based on the total weight of the hot-melt adhesive composition.

The hot-melt adhesive composition of the present invention preferably has a Glass transition temperature (Tg) ranging from 3° C. to 10° C., more preferably from 4° C. to 9.5° C.

A third object of the invention is a method for manufacturing the hot-melt adhesive composition.

A fourth object of the invention is the use of a hot-melt adhesive composition according to the invention for elastic attachment, and in particular for binding an elastic material between two separate substrates.

A fifth object of the invention a laminate comprising at least one elastic material and at least two substrates, said elastic material being inserted between the two substrates and covered with the hot-melt adhesive composition according to the invention.

A sixth object of the invention is a method for manufacturing the laminate according to the invention.

Another object of the invention is a disposable hygiene article comprising at least one laminate according to the invention.

As mentioned above, one of the advantages of the hot-melt adhesive composition according to the invention is that it can be used at high speed line (of at least 400 m/mn) at relatively low temperature (as low as 130° C.) and low pressure, which enables to avoid maintenance issues and downtime production lines.

The hot-melt adhesive according to the invention offers comparable performance to commercial rubber based adhesive and can be used at a temperature below 150° C. (130-140° C.) at high speed (of at least 400 m/mn).

In particular, the hot-melt adhesive composition of the invention is also suitable to be applied at a lower temperature (120° C.) at a lower speed line (200 m/mn), such as on some existing manufacturing lines of disposable hygiene products, as illustrated in the examples.

In particular, the hot-melt adhesive composition of the invention can be applied within a wide process window at a relatively low temperature (130-140° C.) and at a short to long open time (0.2-10 seconds).

Except otherwise expressed in the present application:
the viscosity may be measured using a Brookfield viscometer, at the suitable speed and using the suitable spindle, as known by the person skilled in the art,
the softening point (sp) may be determined by an ASTM Ring and Ball method well known in the art,
the crystallization temperature may be determined by a standard thermal analysis method well known in the art,
the glass transition temperature (Tg) may be measured by Dynamic Mechanical Analysis (DMA) as well known in the art.

Further features and advantages of the invention will appear from the following description of embodiments of the invention, given as non-limiting examples.

BRIEF DESCRIPTION OF THE DRAWING

The FIGURE is given as illustration purpose to help for the comprehension of the invention. The drawing is not to scale. It is a partial representation of a laminate manufacturing process, showing a contact application device comprising of a discharger (9) ended by a contact nozzle (10) equipped with a strand guide (8), which is used to glue a set of elastic strands (3) on a substrate (4) by means of the contact nozzle (10) (Allegro®) having several orifices. The number of orifices of the contact nozzle correspond to the number of elastic strands to be coated by the adhesive composition. The elastic strands are separated and guided by an elastic strand roller (5) and the strand guide (8) so that each elastic strand can be separately coated by the adhesive composition ejected from the orifices of the contact nozzle. The running substrate (4) guided by a roll (6) and the running coated elastic material are put in contact together by means of a roll (7) to form a {substrate+elastic strand} material (11). The {substrate+elastic strand} material is running forward as shown by direction (12) and will be subsequently laminated with another running substrate to form a laminate of two substrate layers comprising in between the elastic strands.

DETAILED DESCRIPTION OF THE INVENTION

Ingredient (A):
The word "thermoplastic styrene block copolymer" (A) (hereinafter noted "SBC (A)", "blend (A)" or "SBC blend (A)") is used in the present application to refer to a blend of thermoplastic styrene block copolymers comprising at least one radial type styrene block copolymer (A1) and at least one styrene diblock copolymer (A2).

The styrene block copolymers included in SBC (A), in particular (A1) and (A2), comprise at least one non elastomeric block A' being a styrene based polymer (preferably polystyrene) and at least one elastomeric block B' being a conjugated diene based block polymer, said conjugated diene based block polymer being preferably non-hydrogenated.

The styrene based polymer is preferably polystyrene. However, the styrene based polymer may also be derived from alkyl substituted styrene monomoners, alkoxy-substituted styrene monomoners and/or mixture thereof with non-substituted styrene monomers. For simplicity herein, the terms referring to styrene, such as "styrene based", "styrene (di)block", "styrene-conjugated diene based block", "styrene content" and the like are preferably intended to include these substituted styrene monomers.

In particular, the radial type SBC (A1) refers to a branched styrene-conjugated diene based block copolymer having a structure in which a plurality of linear type styrene-conjugated diene based block copolymer radially project from a multifunctional center derived from a coupling agent.

The radial type SBC (A1) can be represented by formula (0) below:

$$(A'\text{-}B')_n\text{---}Y\text{---}(B'')_{n'} \qquad (0)$$

wherein:
A' is a non elastomeric block of styrene based polymer, preferably of polystyrene,
B' and B'', identical or different, represent each an elastomeric block of conjugated diene block polymer, said conjugated diene being preferably chosen from butadiene, isoprene and mixture thereof, more preferably butadiene,
—Y is the residue of a multifunctional coupling agent used in the production of the radial type SBC (A1),
n is an integer of at least 3, preferably ranging from 3 to 10, and more preferably from 3 to 5,
n' is an integer ranging from 0 to 10, and preferably from 0 to 4.

Preferably, the radial type SBC (A1) can be represented by formula (1) below:

$$(A'\text{-}B')_n\text{---}Y \qquad (1)$$

wherein:
A' is a non elastomeric block of styrene based polymer, preferably of polystyrene,
B' is an elastomeric block of conjugated diene block polymer, said conjugated diene being preferably chosen from butadiene, isoprene and mixture thereof, more preferably butadiene, —Y is the residue of a multifunctional coupling agent used in the production of the radial type SBC (A1),
n is an integer of at least 3, preferably ranging from 3 to 5.

Each elastomeric and non elastomeric block forming the linear arms (A'-B') of the radial type SBC (A1) may be identical or different. In particular, the average number molecular weight of each elastomeric and non elastomeric block forming the linear type styrene-conjugated diene based block copolymer (A'-B') may vary from one another and may be controlled under a sequential polymerization process well known in the art.

Preferably, the radial type SBC (A1) is a three branched type styrene block copolymer or a four branched type styrene block copolymer, corresponding more preferably to formula (1) wherein B' is an elastomeric block of polybutadiene and n=3 or 4.

The coupling agent is a multifunctional compound which is capable to radially bond several linear type styrene-conjugated diene based block copolymers (corresponding to the arms of the radial type SBC (A1)). There is no particular limitation on the types of the coupling agent which may be used.

Examples of coupling agent include a silane compound such as halogenated silane or alkoxysilane, a tin compound such as halogenated tin, an epoxy compound such as a polycarboxylate ester or epoxydized soybean oil, an acrylic ester such as pentaerythritol tetraacrylate, a divinyl compound such as epoxysilane or divinylbenzene, and the like. Specific examples thereof include trichlorosilane, tribromosilane, tetrachlorosilane, tetrabromosilane, methyltrimethoxysilane, ethyltrimethoxysilane, vinyltrimethoxysilane, vinyltriethoxysilane, tetramethoxysilane, tetraethoxysilane, tetrachlorotin, diethyl adipate, and the like.

The styrene diblock copolymer (A2) (hereinafter noted "diblock (A2)") is a styrene-conjugated diene based diblock copolymer, namely a two-block copolymer comprising one non elastomeric block A' being a styrene based polymer (preferably polystyrene) and one elastomeric block B' being a conjugated diene based polymer block, said conjugated diene based block polymer being preferably non-hydrogenated.

The styrene diblock copolymer (A2) can be represented by formula (2) below:

$$A'\text{-}B' \qquad (2)$$

wherein:

A' is a non elastomeric block of styrene based polymer, preferably of polystyrene, B' is an elastomeric block of conjugated diene block polymer, said conjugated diene being preferably chosen from butadiene, isoprene and mixture thereof, more preferably being butadiene.

The diblock (A2) content in SBC (A) refers to the proportion by weight of styrene diblock copolymer (A2) included in SBC blend (A). Preferably, the diblock (A2) content ranges from 20 to 49% by weight, more preferably from 22 to 45% by weight, based on the total weight of SBC (A).

The styrene content in SBC (A) refers to the proportion by weight of styrene based polymer blocks included in the styrene block copolymers of SBC blend (A). The styrene content may also include the weight proportion of substituted styrene based polymer blocks included in the styrene block polymers of SBC blend (A), when present. Preferably, the styrene content ranges from 30 to 50% by weight, more preferably from 35 to 45% by weight, based on the total weight of SBC (A).

The conjugated diene based block polymers forming the elastomeric blocks of the radial type SBC (A1) and of the diblock (A2) (corresponding to B' in formulas (0), (1) and (2)) are preferably the same. More preferably, SBC (A) is styrene-butadiene based, meaning that the conjugated diene based block polymers forming the elastomeric blocks of the radial type SBC (A1) and of the diblock (A2) are polybutadiene, and thus that in formulas (0), (1) and (2), B' is an elastomeric block of polybutadiene.

The viscosity at 25° C. as a 25% by weight toluene solution refers to the viscosity at 25° C. as a solution having a concentration of 25% by weight using toluene as solvent, and can be measured using various viscometers, for example, a Brookfield type viscometer (at the suitable speed and using the suitable spindle).

Preferably, SBC (A), being more preferably styrene-butadiene based, has:

a viscosity at 25° C. as a 25% by weight toluene solution of more than 250 mPa·s and up to 500 mPa·s, more preferably ranging from 300 to 500 mPa·s, even more preferably ranging from 300 to 450 mPa·s.

The useful SBC (A) may advantageously combine one or several or the above-mentioned features (styrene content, diblock content and/or viscosity) and preferably combine all the above mentioned features.

The useful thermoplastic styrene block copolymer (A) can be prepared from at least one substituted or non-substituted styrene monomer and at least one conjugated diene monomer, using a coupling agent, by any block polymerization method well known in the art to form a mixture of radial type styrene block copolymer and styrene diblock copolymer, as used according to the invention.

The useful SBC (A) are also commercially available. By way of example of useful SBC blends (A) which are commercially available, mention may be made in particular of:

Europrene Sol® T 6414 sold by Eni Versalis Company corresponding to a SBC blend (A) comprising at least one four branched type styrene-butadiene block copolymer and at least one styrene-butadiene diblock copolymer, with a styrene content of about 40% by weight and a diblock content of about 22% by weight, and a viscosity at 25° C. as a 25% by weight toluene solution of 400 mPa·s, and Europrene Sol® T 6434 sold by Eni Versalis Company corresponding to a SBC blend (A) comprising at least one three branched type styrene-butadiene block copolymer and at least one styrene-butadiene diblock copolymer, with a styrene content of about 40% by weight and a diblock content of about 45% by weight, and a viscosity at 25° C. as a 25% by weight toluene solution of 350 mPa·s.

Ingredient (B):

The word "thermoplastic styrene block copolymer" (B) (hereinafter noted "SBC (B)" "blend (B)" or "SBC blend (B)")) is used in the present application to refer to a blend of thermoplastic styrene block copolymers comprising at least one linear type styrene block copolymer (B1) and at least one styrene diblock copolymer (B2).

The styrene block copolymers included in SBC (B), in particular (B1) and (B2), comprise at least one non elastomeric block A' being a styrene based polymer (preferably polystyrene) and at least one elastomeric block X being a conjugated diene based block polymer, said conjugated diene based block polymer being preferably non-hydrogenated.

The styrene based polymer is preferably polystyrene. However, the styrene based polymer may also be derived from alkyl substituted styrene monomoners, alkoxy-substituted styrene monomers and/or mixture thereof with non-substituted styrene monomers. For simplicity herein, the terms referring to styrene, such as "styrene based", "styrene (di)block", "styrene-conjugated diene based block", "styrene content" and the like are preferably intended to include these substituted styrene monomers.

The linear type styrene block copolymer (B1) (hereinafter noted "SBC (B1)") refers to a linear type styrene-conjugated diene based block copolymer of at least three blocks.

In particular, the linear type SBC (B1) can be a triblock SBC of formula (3) or a multiblock SBC of formula (4) below:

$$A'\text{-}X\text{-}A' \qquad (3)$$

$$A'\text{-}(X\text{-}A')_n\text{-}X \qquad (4)$$

wherein:

A' is a non elastomeric block of styrene based polymer, preferably of polystyrene, —X is an elastomeric block of conjugated diene block polymer, said conjugated diene being preferably chosen from butadiene, isoprene and mixture thereof, more preferably butadiene, X being identical or different from B' as defined in formulas (0), (1) and (2), X being identical or different from B" as defined in formulas (0), m is an integer of at least 1.

The styrene diblock copolymer (B2) (hereinafter noted "diblock (B2)") is a styrene-conjugated diene based diblock copolymer, namely a two-block copolymer comprising one non elastomeric block A' being a styrene based polymer (preferably polystyrene) and one elastomeric block X being a conjugated diene based block polymer, said conjugated diene based block polymer being preferably non-hydrogenated.

The styrene diblock copolymer (B2) can be represented by formula (5) below:

A'-X                                                (5)

wherein:

A' is a non elastomeric block of styrene based polymer, preferably of polystyrene, X is an elastomeric block of conjugated diene block polymer, said conjugated diene being preferably chosen from butadiene, isoprene and mixture thereof, more preferably butadiene.

The diblock (B2) content in SBC (B) refers to the proportion by weight of styrene diblock copolymer (B2) included in SBC blend (B). Preferably, the diblock (B2) content ranges from 55 to 80% by weight, more preferably from 60 to 70% by weight, based on the total weight of SBC (B).

The styrene content in SBC (B) refers to the proportion by weight of styrene based polymer blocks included in the styrene block copolymers of SBC blend (B). The styrene content may also include the weight proportion of substituted styrene based polymer blocks included in the styrene block polymers of SBC blend (B), when present. Preferably, the styrene content represents at least 40% by weight, more preferably ranges from 40 to 55% by weight, of the total weight of SBC (B).

The conjugated diene based block polymers forming the elastomeric blocks of the linear type SBC (B1) and of the diblock (B2) (corresponding to X in formulas (3), (4) and (5)) are preferably the same. More preferably, SBC (B) is styrene-butadiene based, meaning that the conjugated diene based block polymers forming the elastomeric blocks of the linear type SBC (B1) and of the diblock (B2) are polybutadiene, and thus that in formulas (3), (4) and (5), B' is an elastomeric block of polybutadiene.

The viscosity at 25° C. as a 25% by weight toluene solution refers to the viscosity at 25° C. as a solution having a concentration of 25% by weight using toluene as solvent, and can be measured using various viscometers, for example, a Brookfield type viscometer (using the suitable spindle).

Preferably, SBC (B), being more preferably styrene-butadiene based, has:

a viscosity at 25° C. as a 25% by weight toluene solution of 200 mPa·s or less, more preferably ranging from 100 to 200 mPa·s.

The useful SBC (B) may advantageously combine one or several or the above-mentioned features (styrene content, diblock content and/or viscosity) and preferably combine all the above mentioned features.

The useful thermoplastic styrene block copolymer (B) can be prepared from at least one substituted or non-substituted styrene monomer and at least one conjugated diene monomer, by any block polymerization method well known in the art to form a mixture of linear type styrene block copolymer and styrene diblock copolymer, as used according to the invention.

The useful SBC (B) are also commercially available. By way of example of useful SBC blends (B) which are commercially available, mention may be made in particular of:

Globalprene® 3545 sold by LCY Chemical Corp Company, corresponding to a SBC blend (B) comprising at least one linear type styrene-butadiene triblock copolymer and at least one styrene-butadiene diblock copolymer, with a styrene content ranging of 43-47% by weight and a diblock content of 60-66% by weight, and a viscosity at 25° C. as a 25% by weight toluene solution of 150 mPa·s, and Asaprene® T439 sold by Asashi Kasei Company, corresponding to a SBC blend (B) comprising at least one linear type styrene-butadiene triblock copolymer and at least one styrene-butadiene diblock copolymer, with a styrene content of about 45% by weight and a diblock content of 60% by weight, and a viscosity at 25° C. as a 25% by weight toluene solution of 170 mPa·s.

Preferably, the conjugated diene based block polymers forming the elastomeric blocks of the radial type SBC (A1), of the linear type SBC (B1) and of the diblocks (A2) and (B2) (corresponding to B' and X in formulas (0) to (5)) are preferably the same. More preferably, SBC (A) and (B) are styrene-butadiene based block copolymers, meaning that the conjugated diene based block polymers forming the elastomeric blocks of the radial type SBC (A1), of the linear type SBC (B1) and of the diblocks (A2) and (B2) are polybutadiene, and thus that in formulas (0) to (5), B' is an elastomeric block of polybutadiene.

SBC (A) and (B) can be mixed in any weight ratio. Preferably, the weight ratio of SBC (A) over SBC (B) ranges from 1 to 2.

The non elastomeric blocks mentioned above in the SBC (A) and (B) have usually a Tg higher than 80° C., and the elastomeric blocks mentioned above in the SBC (A) and (B) have usually a Tg lower than −10° C.

The total amount of SBC (A) and (B) ranges preferably from 15 to 35% by weight, more preferably from 18 to 35% by weight, even more preferably from 20 to 30% by weight, based on the total weight of the hot-melt adhesive composition according to the invention.

Ingredient (C):

The tackifying resin (C) used according to the invention has preferably a softening point up to 120° C., and more preferably ranging from 40° C. to 120° C.

Preferably, the tackifying resin (C) is chosen from:

(i) the homopolymers of terpene resins having a softening point, from about 10° C. to 120° C., the latter polyterpene resins are generally obtained by polymerization of terpene hydrocarbons such as mono-terpene (or pinene), in the presence of Friedel-Crafts catalysts, (ii) the resins obtained by polymerization of alpha-methyl styrene or by copolymerization of alpha-methyl styrene with other hydrocarbon monomers, such as styrene and/or vinyl toluene, said resins may or may not be modified by the action of phenol(s), (iii) phenolic-modified terpene resins such as, for example, the resin product resulting from the condensation, in an acidic medium, of a terpene and a phenol, (iv) rosins of natural or modified origin, such as rosin extracted from pine gum, wood rosin extracted from tree roots and their derivatives, hydrogenated, dimerized, polymerized or esterified by monoalcohols or polyols such as glycerol and pentaerythritol;

(v) aliphatic and cycloaliphatic petroleum derived hydrocarbon resins, the latter resins resulting from the polymerization of monomers consisting primarily of aliphatic or cycloaliphatic olefins and diolefins; also included are the hydrogenated aliphatic and cycloaliphatic petroleum hydrocarbon resins;

(vi) aromatic petroleum derived hydrocarbons resins and the hydrogenated derivatives thereof;

(vii) aliphatic/aromatic petroleum derived hydrocarbons resins and the hydrogenated derivatives thereof;

(viii) and mixture thereof.

According to a preferred embodiment, the tackifying resin (C) used in the hot-melt adhesive composition according to the invention is selected from the tackifying resins of type (v), (vi) and (vii) defined above and mixture thereof. In particular, the tackifying resin (C) is selected from the tackifying resins obtained by hydrogenation, polymerization or copolymerization (with an aromatic hydrocarbon) of mixtures of unsaturated aliphatic hydrocarbons having approximately 5, 9 or 10 carbon atoms, originating from petroleum cuts (usually called C5, C9 or C10 streams from petroleum feedstock).

In particular, the tackifying resins of type (v) are preferably aliphatic (including cycloaliphatic) petroleum hydrocarbon resins (C5 or C10) having a softening point of from about 60° C. to 120° C., said resins resulting usually from the polymerization of C5 or C10-hydrocarbon monomers (or C5 or C10 streams of petroleum feedstock); and the corresponding hydrogenated derivatives resulting from a subsequent total or partial hydrogenation thereof.

In particular, the tackifying resins of type (vi) are preferably aromatic petroleum hydrocarbons resins (C9) having a softening point of from about 60° C. to 120° C., said resins resulting usually from the polymerization of C9-hydrocarbon monomers (or C9 streams of petroleum feedstock); and the corresponding hydrogenated derivatives resulting from a subsequent total or partial hydrogenation thereof.

In particular, the tackifying resins of type (vii) are preferably aliphatic (including cycloaliphatic)/aromatic petroleum resins (C5 or C10/C9) having a softening point of from about 60° C. to 120° C., said resins resulting usually from the polymerization of C5 or C10/C9-hydrocarbon monomers (or C5 or C10 and C9 streams of petroleum feedstock); and the corresponding hydrogenated derivatives resulting from a subsequent total or partial hydrogenation thereof.

As example of C5-hydrocarbon monomers useful to prepare the tackifying resins belonging to class (v) or (vii), mention may be made of trans-1,3-pentadiene, cis-1,3-pentadiene, 2-methyl-2-butene, cyclopentadiene, cyclopentene, and any mixture thereof.

As example of C10-hydrocarbon monomers useful to prepare the tackifying resins belonging to class (v) or (vii), mention may be made of dimers of C5-hydrocarbon monomers, such as dicyclopentadiene.

As example of C9-hydrocarbon monomers useful to prepare the tackifying resins belonging to class (vi) or (vii), mention may be made of vinyltoluenes, dicyclopentadiene, indene, methylstyrene, styrene, methylindenes, and any mixture thereof.

The tackifying resins (C) are commercially available.

In particular, from those of type (i), (ii), (iii) and (iv) defined above, the following products may be mentioned:

resins of type (i): the polyterpene tackifiers from Arizona Chemical company sold under the trade names Sylvagum® TR and Sylvares® TR series (7115, 7125, A25L, B115, M1115), resins of type (ii): Norsolene® W100 available from the company Cray Valley, which is obtained by polymerization of alpha-methyl styrene without the action of phenols; resins of type (iii): Dertophene® 1510 available from the company DRT; Dertophene® H150 available from the same company; Sylvarez® TP 95 available from the company Arizona Chemical, which are phenolic-modified terpene resins;

resins of type (iv): Sylvalite® RE 100 which is an ester of rosin and pentaerythritol available from the company Arizona Chemical, resin of type (v): Escorez® 5400 which is a hydrogenated dicyclopentadiene resin available from Exxon Chemicals with a softening temperature of about 100° C. approximately, resins of type (vi): Regalite® R5100 from Eastman and Wingtack® Extra from Cray-Valley.

In particular, from those of type (v), (vi) and (vii) defined above, the following products may be mentioned:

resins of type (v): Sukorez® SU210 sold by Kolon Company, a partially hydrogenated aliphatic and cycloaliphatic petroleum derived hydrocarbon resin, having a softening point of 110° C. approximately, resins of type (vi): Hikotack® P 90 sold by Kolon Company, a non hydrogenated aromatic petroleum derived hydrocarbon resin, having a softening point of 90° C. approximately, Arkon® M90 sold by Arakawa Company, a partially hydrogenated aromatic hydrocarbon resin, having a softening point of 90° C. approximately, and Arkon® M100 sold by Arakawa Company, a partially hydrogenated aromatic petroleum derived hydrocarbon resin resin, having a softening point 100° C. approximately, resins of type (vii): Quintone® DX390N sold by Zeon Company, a non-hydrogenated aliphatic and aromatic petroleum derived hydrocarbon resin, having a softening point of 90° C. approximately and Sukorez® SU 400 sold by Kolon Company, a hydrogenated aliphatic and aromatic petroleum derived hydrocarbon resin, having a softening point 110° C. approximately.

The hot-melt adhesive composition according to the invention comprises preferably from 35 to 65% by weight, and more preferably from 40 to 65% by weight, of at least one tackifying resin (C), based on the total weight of the hot-melt adhesive composition.

Ingredient (D):

By "wax", it is to be understood a semi-crystalline compound that is solid at room temperature (23° C.) and has an average weight molecular weight of less than 10 000 g/mol.

The wax (D) used according to the invention preferably has a crystallization temperature ranging from 40 to 70° C., more preferably ranging from 40 to 60° C.

The wax (D) used according to the invention preferably has a melting point of 120° C. or less, more preferably ranging from 50 to 120° C.

The wax (D) preferably has a hardness ranging from 3-6 dmm, preferably 4-5 dmm. The hardness expressed in dmm may be measured according to ASTM D-5.

The wax (D) may be chosen from:

(D1) Petroleum wax such as paraffin wax having preferably a melting point (mp) of from about 54° C. to 77° C., microcrystalline wax having preferably a melting point of from about 57° C. to 94° C., or polyolefin based wax;

(D2) Synthetic wax obtained by polymerizing carbon monoxide and hydrogen such as Fischer-Tropsch wax;

(D3) Natural wax corresponding to hydrogenated fats and oils often derived from animal, fish and vegetable, such as hydrogenated tallow, lard, soy oil, hydrogenated cottonseed oil, hydrogenated castor oil, hydrogenated menhaden oil, hydrogenated cod liver oil, which are all solid at room temperature (23° C.) by virtue of their being hydrogenated, and (D4) mixture thereof.

The melting point of wax (D) may be determined by ASTM method D127-60.

Preferably, the useful wax (D) is a polyolefin based wax of (D1) type, and more preferably a polyethylene based wax.

Preferably the polyolefin wax of (D1) type has a melting point ranging from 85° C. to 120° C.

The wax (D) is commercially available. In particular, mention may be made of the following polyethylene based waxes: AC®617 available from Honeywell, LP1020P®, LP1040P® and LP1060P® waxes available from SCG Performance Chemicals Company, and Epolene® available from Westlake Chemical Company.

Preferably, the hot-melt adhesive composition according to the invention comprises from 0.5 to 5% by weight of at least one wax (D), based on the total weight of the hot-melt adhesive composition.

Ingredient (E):

The plasticizer (E) used according to the invention may be chosen from the usual plasticizing oils typically used in SBC based hot melt adhesive compositions to decreased their viscosity, but also the following ones, or mixture thereof: mineral oils, petroleum-derived oils such as paraffinic and naphthenic oils, but also olefin oligomers and low molecular weight polymers, glycol benzoates, as well as non-hydrogenated vegetable and animal oils and derivatives of such oils.

The plasticizer (E) used according to the invention is an amorphous material, which is usually liquid at room temperature (23° C.) or at least at the temperature of use of said plasticizer.

The petroleum-derived oils that may be employed are relatively high boiling temperature materials containing only a minor proportion of aromatic hydrocarbons. In this regard, the aromatic hydrocarbons should preferably be less than 30%, and more particularly less than 15%, by weight, of the oil. Alternately, the oil may be totally non-aromatic.

The olefin oligomers may be polypropylenes, polybutenes, hydrogenated polyisoprenes, hydrogenated polybutadienes, or the like having average weight molecular weights between about 100 and about 10,000 g/mol.

Suitable non-hydrogenated vegetable and animal oils include glycerol esters of the usual fatty acids and polymerization products thereof. Other plasticizers may be used provided they have suitable compatibility with the polymer mixture according to the invention.

The plasticizer (E) preferably used in the hot-melt adhesive composition according to the invention is chosen from petroleum-derived oils, and more preferably from naphthenic and paraffinic oils.

Naphthenic oils and paraffinic oils are petroleum based oils which consist in a mixture of naphthenic hydrocarbons (aliphatic, saturated or unsaturated, C4 to $C_7$-member hydrocarbon rings, and preferably aliphatic, saturated or unsaturated, C4 to $C_6$-member rings cycloalkanes such as cyclopentane, cyclohexane, cycloheptane), paraffinic hydrocarbons (saturated, linear or branched, alkanes) and aromatic hydrocarbons (aromatic hydrocarbon rings, which may be monocyclic or polycyclic, and preferably aromatic $C_6$-member hydrocarbon rings).

The classification of Naphthenic and Paraffinic oils is made based on the amount of each type of hydrocarbons in the oil. Typically, paraffinic oils have a paraffinic hydrocarbons content of at least 50% by weight; naphthenic oils have a naphthenic hydrocarbons content between 30% and 40% by weight, relative to the total weight of the plasticizer.

Preferably the plasticizer(s) (E) used according to the invention is a naphthenic oil.

Useful plasticizers (E) used according to the invention are commercially available. By way of example, mention may be made of the naphtenic oils from Nynas sold under the trade names Nyflex® 223 and Nyflex® 222B, which are preferably used.

Preferably, the hot-melt adhesive composition according to the invention comprises from 5 to 25% by weight of at least one plasticizer (E), based on the total weight of the hot-melt adhesive composition.

Stabilizer:

Preferably at least one stabilizer may be used in the polymer mixture or the hot-melt adhesive composition according to the invention.

The stabilizer includes in particular the antioxidants and ultraviolet absorbers. The useful stabilizers may be any of those usually used in SBC based hot-melt adhesive compositions.

Preferably the antioxidant is chosen from high molecular weight hindered phenols and multifunctional phenols, such as sulfur and phosphorus-containing phenols. Hindered phenols are well known to those skilled in the art and may be characterized as phenolic compounds which also contain sterically hindered radicals in close proximity to the phenolic hydroxyl group thereof. In particular, tertiary butyl groups generally are substituted onto the benzene ring in at least one of the ortho positions relative to the phenolic hydroxyl group. The presence of these sterically hindered substituted radicals in the vicinity of the hydroxyl group serves to retard its stretching frequency and correspondingly, its reactivity; this steric hindrance thus providing the phenolic compound with its stabilizing properties. Representative hindered phenols may include:

1,3,5-trimethyl-2,4,6-tris(3-5-di-tert-butyl-4-hydroxybenzyl)benzene;
pentaerythritoltetrakis-3(3,5-di-tert-butyl-4-hydroxyphenyl) propionate;
n-octadecyl-3(3,5-ditert-butyl-4-hydroxyphenyl)propionate;
4,4'-methylenebis(4-methyl-6-tert butylphenol);
4,4'-thiobis(6-tert-butyl-o-cresol);
2,6-di-tert-butylphenol;
6-(4-hydroxyphenoxy)-2,4-bis(n-ocytlthio)-1,3,5-triazine;
2,4,6-tris(4-hydroxy-3,5-di-tert-butyl-phenoxy)-1,3,5-triazine;
di-n-octadecyl-3,5-di-tert-butyl-4-hydroxybenzylphosphonate;
2-(n-octylthio)ethyl-3,5-di-tert-butyl-4-hydroxybenzoate;
and sorbitol hexa-(3,3,5-di-tert-butyl-4-hydroxy-phenyl) propionate.

The performance of these stabilizers may be further enhanced by utilizing, in conjunction therewith synergists compounds, such as, for example, thiodipropionate esters and phosphites.

A particularly preferred antioxidant is Irganox® 1010, a tetrakis(methylene(3,5-di-teri-butyl-4-hydroxyhydrocinnamate))methane available from BASF.

Preferably, the antioxidant(s) represent(s) from 0.1 to 2% by weight, preferably from 0.3 to 1% by weight, of the polymer mixture according to the invention or of the hot-melt adhesive composition according to the invention.

Other Optional Ingredients:

One or several ingredients other than those described above (also designated as additives), may be used and included either in the polymer mixture according to the invention or in the hot-melt adhesive composition according to the invention.

The optional ingredient(s) may be incorporated in order to modify the particular physical properties of the polymer mixture or of the hot-melt adhesive composition according to the invention.

Among the optional ingredients which may be used, mention may be made of fillers, surfactants, colorants, fluorescent agents, inhibitors of fluorescence, rheology modifiers, and mixture thereof.

The total amount of the optional ingredient(s) which may be present in the polymer mixture according to the invention or the hot-melt adhesive composition according to the invention may range from 0% to 10% by weight, preferably from 0.1% to 5% by weight, and more preferably from 0.1% to 2% by weight, relative to the total weight of the polymer mixture according to the invention or the hot-melt adhesive composition according to the invention.

The polymer mixture according to the invention may be produced by mixing SBC (A) and (B) in a given proportion, optionally mixing stabilizer(s) and/or additive(s), and melting the mixture under stirring. Specifically, the polymer mixture according to the invention is produced by charging the SBC (A) and (B) in a melt-mixing vessel equipped with a twin-screw extruder.

The hot-melt adhesive composition of the present invention may be produced by mixing:
- at least the ingredients of the polymer mixture according to the invention,
- at least one tackifying resin (C),
- at least one wax (D), and
- at least one plasticizer (E). Other optional ingredients as defined above may also be add-mixed.

The present invention thus also relates to a method for manufacturing a hot-melt adhesive composition according to the invention.

In particular, the adhesive composition of the present invention may be produced using any of the techniques known in the art. A representative example of the procedure may involve placing all of the ingredients, except the tackifying resin(s), in a jacketed mixing kettle equipped with rotors, and thereafter raising the temperature of this mixture to a range of 150° C. to 177° C. It should be understood that the precise temperature to be used in this step would depend on the melting point of the particular ingredients. The tackifying resin(s) may subsequently be introduced to the kettle under agitation and the mixing may be allowed to continue until a consistent and uniform mixture is formed. In another embodiment, part of the tackifying resin(s) is first be mixed under heat with all the ingredients, and then the other part of the tackifying resin(s) is subsequently introduced to the kettle under agitation and the mixing is allowed to continue until a consistent and uniform mixture is formed.

The contents of the kettle may be protected with inert gas such as carbon dioxide and nitrogen during the entire mixing process.

The resulting hot melt adhesive composition may then be applied to substrates using a variety of coating techniques.

In particular, the hot-melt adhesive composition according to the present invention may be used for binding an elastic material between two separate substrates, and thus to manufacture a laminate.

The present invention thus also relates to a laminate comprising at least one elastic material and at least two substrates, said elastic material being inserted between two substrates and bonded to them with the hot-melt adhesive composition according to the invention.

By "laminate" it is to be understood a multi-layer material, i.e. a material consisting in at least two layers.

A material is typically considered elastic when it is characterized as having a high percent elastic recovery (i.e., a low percent permanent set) after application of a biasing force. Ideally, elastic materials are characterized by a combination of three temperature independent properties, i.e., a low percent permanent set, and a low percent stress or load relaxation. That is, there should be, (1) no or low relaxing of the stress or unloading while the material is stretched, and (2) complete or high recovery to original dimensions after the stretching, biasing or straining is discontinued. Thus, an elastic material is typically a polymer which, free of diluents, has a break elongation in excess of 100% independent of any crimp (when in fiber form) and which when stretched to twice its length, held for one minute, and then released, retracts to less than 1.5 times its original length within one minute of being released. Such polymers include, but are not limited to, natural rubber or synthetic rubbers, segmented polyurethanes (including polyurethaneureas) such as polyetherurethanes and polyesterurethanes, polyetheresters, elastomeric polyethylenes and polypropylenes, and polyetheramides.

According to an embodiment, the elastic material is chosen from elastomeric fiber, tape, film, strip, coating, ribbon and/or sheet, and, substantially linear ethylene polymers.

As examples of elastic material, mention may be made of spandex (e.g., Lycra® spandex and Lycra® XA, a spandex having little or no lubricating finish thereon). In one embodiment, the elastic material comprises spandex or melt spun elastomers. In another embodiment the elastic material comprises natural or synthetic rubbers in the form of fibers or in the form of strips less than about 10 mm wide.

The U.S. International Trade Commission defines spandex as a manufactured fiber in which the fiber-forming substance is a long-chain synthetic polymer comprised of at least 85 percent by weight of a segmented polyurethane. Lycra® spandex is known to exhibit nearly ideal, temperature independent elastic properties.

According to an embodiment, the elastic material(s) is(are) inserted between a first substrate selected from polyolefin films, such as polyethylene or polypropylene films, and a second substrate selected from non-woven materials, such as non-woven polypropylene or non-woven polyethylene.

According to an embodiment, the laminate of the invention comprises at least two, preferably at least three elastic materials inserted between two substrates.

According to an embodiment of the invention, the elastic material is in the form of a strand of elastic, having preferably a linear density ranging from 235 dtx to 1520 dtx (decitex)

The laminate according to the invention may be manufactured according to a process well known for the skilled person. Document U.S. Pat. No. 6,967,178 describes an example of process for manufacturing a laminate.

A method for manufacturing the laminate according to the invention comprises the following steps:
- providing a first substrate (4),
- providing at least one elastic material (3),
- applying the adhesive composition according to the invention onto at least one elastic material (3), contacting the elastic material(s) covered with the hot-melt adhesive composition according to the invention with the first substrate (4), contacting the second substrate with the elastic material(s), compression between two rollers.

The elastic material is stretched before application of the hot-melt adhesive composition according to the invention, in particular such that the length of the elastic ranges from 2 to 4 times its length at rest (i.e. without stretching), ideally the stretching is performed such that the length of the elastic becomes 3 times longer that the length of the elastic at rest.

Preferably, the hot-melt adhesive composition is applied at a temperature below 150° C., preferably ranging from 130° C. to 140° C., more preferably at a temperature of approximately 130° C.

Preferably, the compression level of the laminates at the nip rolls is about 1 bar.

The open time is defined as the time during which the adhesive composition keeps its adhesive properties. In particular, it corresponds to the time between the application of the adhesive composition on the elastic material and the application of the second substrate thereon.

According to an embodiment, the hot-melt adhesive composition according to the invention has an open time ranging from 0.2 second to 10 seconds, which allows said composition to be used in any conventional high or low speed lines.

Preferably hot-melt adhesive composition has an open time ranging from 0.2 to 2 seconds, which allows said composition to be used in new generation high speed lines (of at least 400 m/mn).

The hot-melt adhesive composition according to the invention may be applied onto the elastic material either by contact applications or non contact applications.

By way of example, coating methods useful to apply the hot-melt adhesive composition according to the invention include roll coating, printing type method, slot coating, extrusion or gun spray coating methods. Spray gun techniques can be done with or without assistance of compressed air that would shape the adhesive spray, and consequently the adhesive pattern. The hot-melt adhesive composition is generally allowed to melt in tanks, and then pumped through hoses to the final coating spot on the substrates.

The hot-melt adhesive composition according to the invention may be applied onto the elastic material continuously or by intermittence. Under continuous application, the adhesive composition, in melted state, is ejected from the nozzle of an application means (hereinafter designated discharger) without interruption and directed to the elastic material to be coated, under the running process. Under intermittent application, the ejection of the melted adhesive composition, which is controlled by the opening of the discharger, is discontinuous. Under this application mode, the discharger is alternatively switched ON and OFF under short period of time.

The nozzle may be of various design and may comprises one of several outlets from which the adhesive composition is intended to be ejected.

The contact application refers to a coating method in which the adhesive nozzle outlet is in contact with the elastic material during the application of the adhesive composition onto the elastic material. The contact application uses a so-called contact nozzle from which the adhesive composition is applied onto the elastic material in a straight way. In the case wherein the elastic material is in the form of a strand, the adhesive composition is applied onto the elastic material in a straight way along the strand. If there are several elastic strands in the laminate, the adhesive composition is applied separately onto each strand. The adhesive pattern thus obtained is a (set of) continuous line(s) that follow the line(s) of the elastic strand(s). The discharger may be connected either to one nozzle having several outlets or to several nozzles in order to apply the adhesive composition simultaneously onto several elastic strands. An example of process for applying the adhesive composition with a contact application is described in document US 2012/0258246. An example of nozzle which may be used for the adhesive contact application is the Allegro® nozzle from Nordson or the SCS® from ITW. The application process may be assisted by air to help the adhesive coating on the elastic material.

Preferably, the amount of the hot-melt adhesive composition applied by contact application method ranges from 10 to 100 mg per linear meter (mg/lm) of one stretched elastic strand, preferably from 20 to 50 mg/lm of one stretched elastic strand. Preferably the ratio of extension of the elastic strand before application of the hot-melt adhesive composition is such that the length of the stretched elastic strand ranges from 2 to 4 times its length at rest (i.e. without stretching), ideally the stretching is performed such that the length of the elastic strand becomes 3 times longer that the length of the elastic strand at rest.

Another advantage of the hot-melt adhesive composition according to the invention is that it is less sensitive to the variation of configuration of the application device than some SBC based hot-melt adhesive compositions of the market. In particular, the hot-melt adhesive composition according to the invention can be applied on the elastic material using a contact application device with a wider scope of contact angle γ Indeed, under contact application process, it was found easier to obtain good adhesive coating and good adhesive pattern with the hot-melt adhesive composition according to the invention, than with an SBC based hot-melt adhesive composition of the market, as the latter one required that the head of the application device and the elastic material to be coated were placed in a specific position to form a specific contact angle γ.

The contact angle γ refers to the angle formed at the intersection of the upper surface of the elastic material where the adhesive composition is intended to be applied and the axis of the discharger body aligned with the nozzle outlet (or orifice) facing the elastic material and from which the adhesive composition is released. A representation of said angle is given in the FIGURE, as illustration purpose, γ corresponding to the sum of the angles α and β, wherein β is the angle formed at the intersection of the upper surface of the elastic material where the adhesive composition is intended to be applied and of the vertical axis (2) which is perpendicular to the ground, and α is the angle formed at the intersection of the axis of the discharger body aligned with the nozzle outlet (1) and the vertical axis (2).

The non contact application refers to a coating method in which the adhesive nozzle outlet is not brought into contact with the elastic material during the application of the adhesive composition onto the elastic material. The non contact application uses a so-called non contact nozzle from which the adhesive composition is applied at a distance from and onto the elastic material. The application process may be assisted by air to help the adhesive to coat the elastic material and/or to form a particular pattern. In several non contact application processes, the adhesive composition is sprayed onto the elastic material. The non contact application process enables to get various type of adhesive pattern designs, which are different from those obtained by contact application process.

Examples of non contact coating method and adhesive patterns which may be obtained by such methods include:

(NC1)—a spiral coating method capable to form an adhesive pattern in spiral form as detailed below, (NC2)—an omega coating method capable to form an adhesive pattern in omega form on the upper surface of the elastic material, (NC3)—a fiberization coating method capable to form an adhesive pattern in wavy and/or short fiber form on the upper surface of the elastic material, (NC4)—a continuous point bonding coating method capable to form an adhesive pattern in dotted-line like form on the upper surface of the elastic material. In this latter method, the coater is usually equipped with a Surewrap® nozzle from Nordson.

The spiral application (NC1) comprises the application of the adhesive composition which is ejected from a nozzle and deflected by an air flow before application to the elastic material(s) so that said adhesive composition is applied by forming a spiral on the upper surface of the elastic material. If there are several elastic strands in the laminate, the adhesive composition is applied in one step onto several elastic strands. For example, if the laminate comprises three elastic strands, one nozzle may apply simultaneously by spraying the adhesive composition onto the three strands. It is also possible having more than three strands, such as six or nine strands and in those cases, several nozzles may apply the adhesive composition onto several strands by spiral application.

The coating method of (NC4) type is preferred to coat elastic strands at high speed with a low add-on level of adhesive composition, compared to spiral application method (NC1). In this preferred coating method, the adhesive composition is ejected from a set of holes of the nozzle. Each elastic strand is maintained at a close distance of each orifice by a strand guide, and so that to each hole of the nozzle faces an elastic strand. The adhesive composition ejected from each nozzle orifice is then deflected by the application of an air flow before application of the adhesive composition to the elastic strand facing said orifice, so that said adhesive composition partially wraps each elastic strand by spinning around each individual elastic strand. The adhesive pattern thus obtained is a set of dotted lines that follow the lines of the elastic strands (when sawn from the top view of the elastic strands). An example of nozzle for the dot bond application is the Surewrap® nozzle from Nordson.

For spiral coating method (NC1), the amount of the hot-melt adhesive composition applied by such method ranges preferably from 5 to 100 g/m², preferably from 10 to 50 g/m², even more preferably from 10 to 20 g/m². The amount of the hot-melt adhesive composition is preferably expressed in gram per square meter (gsm) of the substrate onto which the elastic material is contacted and the adhesive is intended to be applied.

For coating method of (NC4) type, the amount of the hot-melt adhesive composition applied by such method ranges preferably from 10 to 100 mg per linear meter (mg/lm) of one stretched elastic strand, preferably from 20 to 50 mg/lm of one stretched elastic strand. Preferably the ratio of extension of the elastic strand before application of the hot-melt adhesive composition is such that the length of the stretched elastic ranges from 2 to 4 times its length at rest (i.e. without stretching), ideally the stretching is performed such that the length of the elastic becomes 3 times longer that the length of the elastic at rest.

For the other above-mentioned non coating methods, the amount of the hot-melt adhesive composition applied may be any conventional amount used in the art.

In the contact or non contact application method, the ON/OFF parameters to be set under intermittent mode can be determined depending on the type of hygiene disposable product to manufacture, and in particular the length of the substrate where the adhesive composition should be applied. "OFF" means that the adhesive composition is not applied on the substrate, "ON" means that the adhesive composition is applied on the substrate. In particular, for baby diapers, the intermittent mode is usually set at 29 cm OFF/33 cm ON, meaning that the adhesive composition is applied on a 33 cm length area every 62 cm length of the substrate, and each adhesive coated areas being spaced by a 29 cm length non coated area. For adult diapers, the adhesive composition would be applied on a longer part of substrate.

According to an embodiment of the invention, the hot-melt adhesive composition according to the invention has a viscosity, measured at 121° C. of 20 000 mPa·s. or less, preferably ranging from 15000 to 20 000 mPa·s.

Preferably, the hot-melt adhesive composition has a viscosity, measured at 135° C. of 10 000 mPa·s. or less, preferably of 9 000 or less, and a glass transition temperature Tg ranging from 1° C. to 15° C., preferably from 4° C. to 10° C., which contributes to the advantages of the hot-melt adhesive composition according to the invention of being particularly easy to process and to use.

Another object of the invention is a disposable article comprising the laminate according to the invention.

The disposable article is preferably a disposable hygiene article, preferably chosen from diapers, training pants, absorbent underpants, adult incontinence products, feminine hygiene products, and the like.

EXAMPLES

The adhesive compositions of examples 1 to 5 according to the invention and the adhesive compositions of the comparative examples CE1 to CE3, disclosed below, were compared as regards their physical properties and their performances.

The adhesive compositions of the comparative examples CE1, CE2 and of the examples 1 to 5 according to the invention were prepared by mixing the ingredients indicated in table 1, following a process as described above in the detailed description. The amount of each ingredient used in Table 1 are expressed in percentage by weight based on the total weight of each adhesive composition. In particular, the adhesive composition of the comparative example CE1 comprises a SBC (B), but no SBC (A), the total amount of SBC representing 23% by weight of the total weight of the adhesive composition, the adhesive composition of the comparative example CE2 comprises a SBC (A), but no SBC (B), the total amount of SBC representing about 23% by weight of the total weight of the adhesive composition.

the adhesive composition of the comparative example CE3 corresponds to a SBC based adhesive composition sold by Bostik SA comprising about 23% by weight based on the total weight of the adhesive composition, of a SBC being different from SBC (A) and (B).

The following ingredients were used in Table 1:

As SBC Blend Comprising at Least One Radial Type SBC:
  Europrene Sol® T 6414 and Europrene Sol® T 6434 sold by Eni Versalis Company, corresponding each to a SBC (A), As SBC Blend Comprising at Least One Linear Type SBC:
  Globalprene® 3545 sold by LCY Chemical Corp Company and Asaprene® T439 sold by Asashi Kasei Company, corresponding each to a SBC (B),
  Taipol® 4202 sold by TSRC Corporation Company, being different from a SBS (B) and corresponding to a linear type styrene-butadiene block copolymer with a styrene content of 40% by weight, but no diblock, and having a viscosity at 25° C. as a 25% by weight toluene solution of 620 mPa·s;

As Tackifying Resin:
  Sukorez® SU210 sold by Kolon Company, corresponding to a tackifying resin (C) of type (v),
  Quintone® DX390N sold by Zeon Company, corresponding to a tackifying resin (C) of type (vii),
  Sukorez® SU 400 sold by Kolon Company, corresponding to a tackifying resin (C) of type (vii),
  Hikotack® P 90 sold by Kolon Company, corresponding to a tackifying resin (C) of type (vi),
  Arkon® M90 sold by Arakawa Company, corresponding to a tackifying resin (C) of type (vi);

As Wax:
  LP1020P® wax available from SCG Performance Chemicals Company, a polyethylene homopolymer wax (D);

As Plasticizer:
  Nyflex® 223 sold by Nynas, a naphthenic oil (E);

As Stabilizer:
  Irganox® 1010 sold by BASF, a phenolic hindered antioxidant.

TABLE 1

| Ingredients | Ex1 | Ex2 | Ex3 | Ex4 | Ex5 | CE1 | CE2 |
|---|---|---|---|---|---|---|---|
| Europrene Sol ® T 6414 | 15 | — | 15 | — | 14 | — | 23 |
| Europrene Sol ® T 6434 | — | 15 | — | 15 | — | — | — |
| Globalprene ® 3545 | — | — | 8.8 | 8.8 | 10 | — | — |
| Asaprene ® T439 | 8.8 | 10 | — | — | — | 15 | — |
| Taipol ® 4202 | — | — | — | — | — | 8.8 | — |
| Sukorez ® SU210 | 42 | 41 | 52.6 | 52.6 | 34 | 42 | 40.9 |
| Quintone ® DX390N | 12.6 | 12.4 | — | — | — | 12.6 | 12.2 |
| Sukorez ® SU 400 | — | — | — | — | 18 | — | 4 |
| Hikotack ® P 90 | — | — | 6 | 6 | 6 | — | — |
| Arkon ® M90 | 4 | 4 | — | — | — | 4 | — |
| LP1020P ® wax | 2 | 2 | 2 | 2 | 2.3 | 2 | 4.3 |
| Nyflex ® 223 | 15.1 | 15.1 | 15.1 | 15.1 | 15.2 | 15.1 | 15.1 |
| Irganox ® 1010 | 0.5 | 0.5 | 0.5 | 0.5 | 0.5 | 0.5 | 0.5 |
| Total | 100 | 100 | 100 | 100 | 100 | 100 | 100 |

Physical Properties of the Hot-Melt Adhesive Compositions:

The viscosity of each adhesive composition has been measured at different temperatures using a Brookfield viscometer at suitable speed and using the suitable spindle, as known in the art.

The Glass transition temperature (Tg) or the temperature corresponding to the maximum of damping factor (Tango), has been measured by Dynamic Mechanical Analysis (DMA) in strain controlled mode (1%) and a temperature ramp of 6° C./mn at frequency sweep of 1 Hz.

The results of these measurements are given in Table 2 below.

TABLE 2

| Physical properties | | Ex1 | Ex2 | Ex3 | Ex4 | Ex5 | CE1 | CE2 | CE3 |
|---|---|---|---|---|---|---|---|---|---|
| Viscosity (mPa · s.) | at 121° C. | 16900 | 18200 | 19000 | 19900 | 16800 | 12100 | 18900 | 29100 |
| | at 135° C. | 6850 | 7400 | 7800 | 7850 | 7200 | 5000 | 7700 | 12100 |
| | at 149° C. | 3500 | 3930 | 4050 | 3980 | 3500 | 3200 | 3800 | 7350 |
| Tg (° C.) | | 6 | 4 | 9.5 | 9 | 7.5 | 9.5 | 3.5 | 7 |

Creep Resistance:

Preparation of the Laminates Under Allegro® Contact or Surewrap® Non Contact Application Process:

Laminated specimens for creep resistance tests were prepared by laminating three elastic strands (T837 Lycra Hyft® Fiber) stretched to 300% between one layer of spunbond polypropylene (PP) non woven fabric of 14 g/m² basis weight and one breathable polyethylene (PE) film of 20 μm thickness, by applying the adhesive composition using Nordson CLT4400 coater, as follows.

The Nordson CLT4400 coater used was equipped either with a contact nozzle (Allegro®) which enable 3 strands coating, or with non-contact nozzle (Surewrap®) which enable 3 strand coating, and worked under the following conditions:

Line speed=500 m/mn,
  Application temperature=130° C. or 140° C.,
  Intermittent mode=29 cm OFF/33 cm ON,
  Time between the application of the adhesive composition on the elastic material and the application of the second substrate thereon=0.2 s,
  Compression at the nip rolls=1 bar,
  Adhesive add-on level=30 mg/lm/strand.

The laminates were made as follows: The substrates and the elastic strands were guided by rolls and runned a laminator speed rate of 500 m/mn on the laminate production line. The strands of the elastic material were stretched with a ratio of extension of 1:4 before being coated by the hot-melt adhesive composition by means of the contact or non-contact nozzle. The hot-melt adhesive composition was applied at 130° C. or 140° C. on each strands. The coated elastic strands were then put in contact with a first substrate (non woven PP) under the running process. Then a second substrate (PE) was applied on the running superimposed substrate and coated stretched elastic strands (hereinafter noted {substrate+elastic strands} so that the coated elastic strands are in sandwich between the first and second substrate. At last, the overall multilayer material was compressed under a 1 bar compression through nip rolls.

Preparation of the Laminates Under Spiral Non Contact Application Process:

The preparation of the laminates is the same as described above, except that the Nordson CLT4400 coater used was equipped with a CFO spray nozzle (control fiberization spray nozzle), available from Nordson and worked under the following conditions:

Line speed=200 m/mn,
Application temperature=120° C., 130° C. or 140° C.,
Intermittent mode=29 cm OFF/33 cm ON,
Time between the application of the adhesive composition on the elastic material and the application of the second substrate thereon=0.9 s,
Compression at the nip rolls=1 bar,
Adhesive add-on level=15 or 25 gsm.

The laminates were made as follows: The substrates and the elastic strands were guided by rolls and runned a laminator speed rate of 200 m/mn on the laminate production line. The strands of the elastic material were stretched with a ratio of extension of 1:4 before being coated by the hot-melt adhesive composition by means of the non contact spiral nozzle. The hot-melt adhesive composition was sprayed at 120° C., 130° C. or 140° C. on the elastic strands and a first substrate (non woven PP) at the point where the elastic strand will be in contact with the first running substrate. Then a second substrate (PE) was applied on the running superimposed substrate and coated stretched elastic strands (hereinafter noted {substrate+elastic strands} so that the coated elastic strands are in sandwich between the first and second substrate. At last, the overall multilayer material was compressed under a 1 bar compression through nip rolls.

Pumping Pressure

The pumping pressure of the Nordson CLT4400 coater was measured with a manometer, while the adhesive composition was coated on the elastic strands using a contact or non-contact nozzle. A measured pressure below 60 bar is desirable. The results are given in Table 3 below, expressed in bar.

TABLE 3

| | Pumping pressure (Bar) | | | | | |
|---|---|---|---|---|---|---|
| | Ex1 | Ex3 | Ex5 | CE1 | CE2 | CE3 |
| Allegro ® at 130° C. | 45 | 30 | 45 | 40 | 45 | 65 |
| Allegro ® at 140° C. | 35 | 25 | 35 | 35 | 35 | 50 |
| Surewrap ® at 130° C. | 55 | 55 | 55 | 50 | 50 | >65 |
| Surewrap ® at 140° C. | 40 | 50 | 45 | 40 | 42 | 60 |
| CF ® Spray at 120° C., 130° C., 140° C. | *** | *** | <<60 | *** | *** | *** |

It was observed that all the adhesive compositions according to the invention (ex 1, 3 and 5) were suitable for all the tested application processes.

On the opposite, it was observed that the adhesive composition of comparative example CE3 does not fit with the requirement of contact and non contact application processes at 130° C. and for non contact process at 140° C., running at high speed line, as the pumping pressure of said composition in the coater was equal or exceed the maximum pressure tolerated (60 bar).

Quality of Adhesive Patterns

The quality of the adhesive pattern obtained was assessed using an Ultraviolet light to visualize the adhesive coating pattern, on 6 laminate specimens as prepared above.

The quality of the adhesive pattern obtained was rated from 1 to 4, as detailed below, 1 rating for the lowest quality of the adhesive pattern and 4 rating for the best quality of the adhesive pattern:

1=the adhesive pattern is too bad: meaning that on the specimen obtained by the application process using:
  Surewrap®, none of the dots form a dotted line pattern,
  Allegro®, at least one of the expected continuous lines is broken (or discontinuous) at several points,
  CFO Spray, no spiral pattern are obtained,
2=the adhesive pattern is not good: meaning that on the specimen obtained by the application process using:
  Surewrap®, some dotted lines were observed, out of the three expected ones,
  Allegro®, at least one of the continuous lines have an irregular width (or line thickness),
  CFO Spray, the continuous line of the spirals presents spirals of irregular form or having unproper width,
3=the adhesive pattern is good, but still has defects: meaning that on the specimen obtained by the application process using:
  Surewrap®, three dotted lines were observed, but with some imperfections on at least one start/end of the line, due in particular to adhesive build up and/or scattering problems,
  Allegro®, at least one of the homogeneous continuous lines has some imperfections on at least one start/end of the line, due in particular to build up and/or pressure problems,
  CFO Spray, the continuous line of the spirals presents spirals of regular form and regular line thickness, but has some imperfections on at least one start/end of the spiral line, due in particular to adhesive scattering, build up and/or pressure problems,
4=the adhesive pattern is perfect, meaning that on the specimen obtained by the application process using:
  Surewrap®, three dotted lines were observed, with neat start and cut-off at the ends of the lines,
  Allegro®, three continuous lines of regular and identical line thickness were observed, with neat start and cut-off at the ends of the lines,
  CFO Spray, the continuous lines of having identical spirals of good size and regular and identical line thickness was observed, with neat start and cut-off at the ends of the spiral pattern.

An average mark was given from the 6 assessed laminates. The average marks were recorded in Table 4 below. An average mark above 3 is desirable.

TABLE 4

| | Ranking of the quality of the adhesive patterns | | | | | |
|---|---|---|---|---|---|---|
| | Ex1 | Ex3 | Ex5 | CE1 | CE2 | CE3 |
| Allegro ® at 130° C. | 4 | 3.5 | 4 | 4 | 3.5 | 2 |
| Allegro ® at 140° C. | 4 | 3.5 | 4 | 4 | 3.5 | 2 |
| Surewrap ® at 130° C. | 3.5 | 3.5 | 4 | 3.5 | 3 | 1 |
| Surewrap ® at 140° C. | 4 | 4 | 4 | 4 | 3.5 | 2 |
| CF ® Spray at 130° C. (15 gsm) | *** | *** | above 3 and up to 4 | *** | *** | *** |

It was observed that all the adhesive composition according to the invention (ex 1, 3 and 5) lead to good adhesive patterns for all the tested application processes. In particular, it was observed that the same quality of pattern was obtained for the adhesive composition of example 5 according to the invention applied on a conventional low speed coating process.

On the opposite, it was observed that the adhesive composition of comparative example CE3 does not apply correctly at high line speed and does not provide good patterns by either using contact or non contact application process, at an application temperature of 130° C. and 140° C.

Measurement of the Creep Resistance

The creep resistance of the laminated specimens was measured as follows, using the adhesive composition of examples 1, 3 and 5 according to the invention and comparative examples CE1, CE2 and CE3.

Specimen, prepared as described above, of total length of 91 cm (29 cm non bonded+33 cm bonded+29 cm non bonded) is cut. The wrinkles, corresponding to the start and end of the sandwiched elastic strands in the prepared laminate (hereafter noted NW+Elastic+adhesive+PE film), are then marked to identify the start and end of bonded elastics. The specimen is then attached at one of its ends (hereafter noted NW+PE), by the tips to a rectangular piece of rigid Plexiglas, so as not to attach the elastic strands. The laminate (Nw+Elastic+adhesive+PE film) is then stretched out completely and the other end of the specimen (Nw+PE) is securely attached on the same Plexiglas board, by its tips so as not to attach the elastic strands. The initial length between the marks is then measured with a ruler. This distance is noted d0. The overall Plexiglas board and laminate is then placed in an air-circulating oven at 38° C. Under these conditions, the elastic strands under stress can retreat to a certain distance. After 4 hours, the Plexiglas board is taken out from the oven and the specimens are detached from the Plexiglas and allowed to relax.

As the elastic strands are allowed to retreat, the bonded part (Nw+Elastic+adhesive+PE film) will retract and lead again to the formation of wrinkles. The beginning and end of the new wrinkles are then marked. Then, the laminate is fully stretched again and the distance between the new marks is measured with a ruler on the stretched specimen. This distance is noted d. The Creep Resistance or bond retention is calculated by the formula:

% creep resistance=100−[(d0−d)×100/d0]

The results were averaged for 6 tested specimens and recorded in Table 5 below. An average Creep Resistance of at least 75% is desirable.

The above described test was performed at different times and temperatures storage conditions after the preparation of the laminated specimens:

Initial: 24 hours after the preparation of the laminated specimens,
2 weeks @ 23° C.: after 2 weeks of storage at 25° C. of the laminated specimens,
2 weeks @ 55° C.: after 2 weeks of storage at 55° C. of the laminated specimens,
4 weeks @ 23° C.: after 4 weeks of storage at 25° C. of the laminated specimens,
4 weeks @ 55° C.: after 4 weeks of storage at 55° C. of the laminated specimens.

TABLE 5

Average creep resistance

| | | EX1 | EX3 | EX5 | CE1 | CE2 | CE3 |
|---|---|---|---|---|---|---|---|
| Allegro ® at 130° C. | Initial | 86.8 | 85.3 | 85.5 | 81.8 | 77.3 | 78.9 |
| | 2 weeks @ 23° C. | 86.3 | 85.7 | 88.8 | 79.6 | *** | 83.3 |
| | 2 weeks @ 55° C. | 87.2 | 74.5 | 83.9 | 48.8 | 62.0 | 73.4 |
| | 4 weeks @ 23° C. | 84.3 | 83.0 | 82.2 | ** | 64.0 | 80.0 |
| | 4 weeks @ 55° C. | 80.2 | 71.3 | 84.6 | ** | 69.0 | 67.2 |
| Allegro ® at 140° C. | Initial | 91.2 | 91.8 | 90.1 | 77.0 | 74.8 | 86.6 |
| | 2 weeks @ 23° C. | 89.8 | 86.2 | 86.1 | 68.0 | *** | 84.5 |
| | 2 weeks @ 55° C. | 86.3 | *** | 85.9 | 0 | 60.0 | 84.9 |
| | 4 weeks @ 23° C. | 87.1 | 85.9 | *** | ** | 63.0 | 85.2 |
| | 4 weeks @ 55° C. | 81.9 | 81.0 | 90.0 | ** | 60.0 | 80.3 |
| Surewrap ® at 130° C. | Initial | 86.4 | 83.5 | 88.5 | 84.0 | 87.0 | * |
| | 2 weeks @ 23° C. | 86.7 | *** | 85.3 | 85.7 | *** | * |
| | 2 weeks @ 55° C. | 80.1 | 88.6 | 84.6 | 65.3 | 83.0 | * |
| | 4 weeks @ 23° C. | 87.5 | 87.3 | 90.2 | ** | 90.7 | * |
| | 4 weeks @ 55° C. | 82.5 | 91.0 | 88.0 | ** | 82.8 | * |
| Surewrap ® at 140° C. | Initial | 90.9 | 87.0 | 90.1 | 92.5 | 85.5 | 88.7 |
| | 2 weeks @ 23° C. | 92.7 | 83.5 | 92.7 | 93.1 | *** | 89.4 |
| | 2 weeks @ 55° C. | 89.8 | *** | 86.3 | 90.9 | 89.6 | 85.9 |
| | 4 weeks @ 23° C. | 88.8 | 84.5 | 89.56 | *** | 95.3 | 83.4 |
| | 4 weeks @ 55° C. | 85.7 | 82.6 | 85.9 | *** | 94.0 | 77.9 |
| CF ® Spray at 120° C. (15 gsm) | Initial | *** | *** | 91.3 | *** | *** | *** |
| | 4 weeks @ 23° C. | *** | *** | 94.1 | *** | *** | *** |
| | 4 weeks @ 55° C. | *** | *** | 82.1 | *** | *** | *** |
| CF ® Spray at 120° C. (25 gsm) | Initial | *** | *** | 90.1 | *** | *** | *** |
| | 4 weeks @ 23° C. | *** | *** | 90.4 | *** | *** | *** |
| | 4 weeks @ 55° C. | *** | *** | 83.4 | *** | *** | *** |
| CF ® Spray at 130° C. (15 gsm) | Initial | *** | *** | 91.9 | *** | *** | *** |
| | 4 weeks @ 23° C. | *** | *** | 93.4 | *** | *** | *** |
| | 4 weeks @ 55° C. | *** | *** | 86.3 | *** | *** | *** |
| CF ® Spray at 130° C. (25 gsm) | Initial | *** | *** | 91.3 | *** | *** | *** |
| | 4 weeks @ 23° C. | *** | *** | 93.1 | *** | *** | *** |
| | 4 weeks @ 55° C. | *** | *** | 91.3 | *** | *** | *** |
| CF ® Spray at 140° C. (15 gsm) | Initial | *** | *** | 92.8 | *** | *** | *** |
| | 4 weeks @ 23° C. | *** | *** | 93.3 | *** | *** | *** |
| | 4 weeks @ 55° C. | *** | *** | 94.3 | *** | *** | *** |
| CF ® Spray at 140° C. (25 gsm) | Initial | *** | *** | 91.1 | *** | *** | *** |
| | 4 weeks @ 23° C. | *** | *** | 93.6 | *** | *** | *** |
| | 4 weeks @ 55° C. | *** | *** | 94.7 | *** | *** | *** |

* It was not possible to prepare elastic attachment samples due to the poor adhesive coatability at 130° C. (bad wrapping of elastics and bad cut-off).
** Due to the low bond retention value of earlier tests, aged elastic creep resistance were not measured.
*** Not measured On Contact Application High Speed Process Using Allegro®:

It was observed that all the laminates made from the adhesive compositions of examples 1, 3 and 5 according to the invention under the high speed rate contact application process at 130° C. and 140° C., present better creep resistance compared to those made from the adhesive compositions of comparative examples CE1 to CE3, at initial or after the above described different storage conditions.

It was also observed that the adhesive performance of the hot-melt adhesive compositions according to the invention were maintained over time at a satisfactory level (creep resistance above 70%) after storage at room temperature (23° C.) or after ageing of the laminates.

On the opposite, it was observed that the creep resistance of the adhesive compositions of comparative examples CE1 and CE2 applied at 130° C. or 140° C. significantly dropped after 2 weeks of storage at 23° C. or 55° C., resulting in a non-satisfactory creep resistance.

It was also observed that the creep resistance of the adhesive compositions of comparative example CE3 applied at 130° C. dropped after 4 weeks of storage at 55° C., resulting in a non-satisfactory creep resistance.

Therefore, the adhesive performance of the comparative compositions were degraded over time so that the creep resistance is no more satisfactory to provide a good elastic attachment.

On Non Contact Application High Speed Process Using Surewrap®:

It was observed that all the laminates made from the adhesive compositions of examples 1, 3 and 5 according to the invention under the high speed rate non contact application process at 130° C. and 140° C., present similar or better creep resistance compared to those made from the adhesive compositions of comparative examples CE1 to CE3, at initial or after the above described different storage conditions. In particular, it was observed that the adhesive composition of comparative example CE3 could not be applied at 130° C. under the high speed rate non contact application process using Surewrap®.

It was also observed that the adhesive performance of the hot-melt adhesive according to the invention were maintained over time at a satisfactory level (creep resistance above 70%) after storage at room temperature or ageing of the laminates.

On the opposite, it was observed that the creep resistance of the adhesive compositions of comparative example CE1 applied at 130° C. significantly dropped after 2 weeks of storage at 55° C., resulting in a non-satisfactory creep resistance.

On Conventional Non Contact Spiral Application Process Using CF® Spray Nozzle Application:

It was observed that the laminate made from the adhesive composition of example 5 according to the invention applied under a conventional low speed non contact application process, presents excellent creep resistance over time.

CONCLUSIONS

Therefore, only the adhesive compositions according to the invention displayed both good initial and aged (i.e. after storage) creep performance, under the overall tested process and conditions.

In view of the all the various tests performed, it was thus shown that only the adhesive compositions according to the invention present an excellent balance of good processability, good pattern control and good adhesive performance, whatever the application process used (fast speed production lines at low application temperature or conventional ones).

The invention claimed is:

1. A polymer mixture comprising:
   at least one thermoplastic styrene block copolymer (A) comprising at least one radial type styrene block copolymer (A1) and at least one styrene diblock copolymer (A2), said thermoplastic styrene block copolymer (A) having:
      a styrene content of at least 30% by weight, and
      a non-zero diblock content of less than 50% by weight, based on the total weight of said thermoplastic styrene block copolymer (A),
   at least one thermoplastic styrene block copolymer (B) comprising at least one linear type styrene block copolymer (B1) and at least one styrene diblock copolymer (B2), said thermoplastic styrene block copolymer (B) having:
      a styrene content of at least 35% by weight, and
      a diblock content of at least 50% by weight, based on the total weight of said thermoplastic styrene block copolymer (B),
      wherein a weight ratio of the at least one thermoplastic styrene block copolymer (A) to the at least one thermoplastic styrene block copolymer (B) ranges from 1 to 2.

2. The polymer mixture according to claim 1, wherein the thermoplastic styrene block copolymer (A) has a styrene content ranging from 30 to 50% by weight.

3. The polymer mixture according to claim 1, wherein the thermoplastic styrene block copolymer (A) has a diblock content ranging from 20 to 49% by weight.

4. The polymer mixture according to claim 1, wherein the thermoplastic styrene block copolymer (B) has a styrene content of at least 40% by weight.

5. The polymer mixture according to claim 1, wherein the thermoplastic styrene block copolymer (B) has a diblock content ranging from 55 to 80% by weight.

6. The polymer mixture according to claim 1, wherein the thermoplastic styrene block copolymers (A) and (B) are styrene-butadiene based block copolymers.

7. The polymer mixture according to claim 1, wherein the thermoplastic styrene block copolymer (A) has a viscosity at 25° C. as a 25% by weight toluene solution of more than 250 mPa·s and up to 500 mPa·s.

8. The polymer mixture according to claim 1, wherein the thermoplastic styrene block copolymer (B) has a viscosity at 25° C. as a 25% by weight toluene solution of 200 mPa·s or less.

9. A hot-melt adhesive composition comprising:
   at least the ingredients of the polymer mixture as defined in claim 1,
   at least one tackifying resin (C),
   at least one wax (D), and
   at least one plasticizer (E).

10. The hot-melt adhesive composition according to claim 9, comprising:
    from 40 to 65% by weight of the at least one tackifying resin (C),
    from 0.5 to 5% by weight of the at least one wax (D), and
    from 5 to 25% by weight of the at least one plasticizer (E), based on the total weight of the hot-melt adhesive composition.

11. The hot-melt adhesive composition according to claim 9, wherein the total amount of the thermoplastic styrene block copolymers (A) and (B) ranges from 15 to 35% by weight, based on the total weight of the hot-melt adhesive composition.

13. A laminate comprising at least one elastic material and at least two substrates, the laminate configured such that said elastic material is disposed between the two substrates and covered with the hot-melt adhesive composition according to claim 9.

13. A disposable hygiene article comprising at least one laminate according to claim 12.

* * * * *